(12) United States Patent
Hatori

(10) Patent No.: US 7,777,892 B2
(45) Date of Patent: Aug. 17, 2010

(54) TOMOGRAPHY SYSTEM AND METHOD OF ADJUSTING QUALITY OF IMAGE OBTAINED BY OPTICAL TOMOGRAPHY SYSTEM

(75) Inventor: Masami Hatori, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 213 days.

(21) Appl. No.: 11/723,617

(22) Filed: Mar. 21, 2007

(65) Prior Publication Data
US 2007/0237445 A1 Oct. 11, 2007

(30) Foreign Application Priority Data
Mar. 22, 2006 (JP) ............................. 2006-078531

(51) Int. Cl.
*G01B 9/02* (2006.01)
(52) U.S. Cl. ...................... 356/497; 356/479; 356/495
(58) Field of Classification Search ................. 356/479, 356/497, 495, 487
See application file for complete search history.

(56) References Cited

U.S. PATENT DOCUMENTS

| | | | | |
|---|---|---|---|---|
| 5,459,570 | A | * | 10/1995 | Swanson et al. ............. 356/479 |
| 5,987,195 | A | * | 11/1999 | Blake ........................... 385/12 |
| 6,674,514 | B2 | * | 1/2004 | Shinoda ....................... 355/71 |
| 7,564,565 | B2 | * | 7/2009 | Shimizu et al. ............. 356/497 |
| 2007/0086017 | A1 | * | 4/2007 | Buckland et al. ............ 356/497 |

FOREIGN PATENT DOCUMENTS

| | | |
|---|---|---|
| JP | 2000-97845 A | 4/2000 |
| JP | 2000-126188 A | 5/2000 |
| JP | 2000-262461 A | 9/2000 |

OTHER PUBLICATIONS

Mitsuo Takeda, "Optical Frequency Scanning Interference Microscopes", Optics Engineering Contact, 2003, pp. 426-432, vol. 41, No. 7, and its Partial English Translation.

* cited by examiner

*Primary Examiner*—Hwa S. A Lee
(74) *Attorney, Agent, or Firm*—Sughrue Mion, PLLC

(57) ABSTRACT

In an optical tomography system, a polarization changing system which converts linearly polarized light too non-linearly polarized light is provided in at least one of a light source unit, an optical path from the light source unit to a light dividing system, the optical path of the measuring light from the light dividing system to an object, the optical path of the reflected light from the object to the combining system and the optical path of the reference light from the light dividing system to the combining system. The polarization changing system is, for instance, a polarization-preserving optical fiber which is disposed so that the direction of polarization of the linearly polarized light and the direction of axis of polarization of the linearly polarized light differ from each other.

6 Claims, 11 Drawing Sheets

TOMOGRAPHY SYSTEM AND METHOD OF ADJUSTING QUALITY OF IMAGE OBTAINED BY OPTICAL TOMOGRAPHY SYSTEM

BACKGROUND OF THE INVENTION

1. Field of the Invention

This invention relates to an optical tomography system for obtaining an optical tomographic image by measurement of OCT (optical coherence tomography) and a method of adjusting quality of an image obtained by a tomography system.

2. Description of the Related Art

When obtaining tomographic images of living tissue, there has sometimes been used optical tomography systems employing OCT measurement. In such an optical tomography system, low coherence light emitted from a light source is divided into measuring light and reference light and the measuring light is projected onto the object of measurement, while the reflected light from the object of measurement when the measuring light is projected onto the object is combined with the reference light, and a tomographic image is obtained on the basis of the intensity of the interference light of the reflected light and the reference light. See, for instance, Japanese Unexamined Patent Publication Nos. 2000-097845, 2000-126188 and 2000-262461.

In the optical tomography system, there are also known systems using the TD-OCT (time domain OCT) measurement, where the measuring position in the depth direction of the object is changed by changing the optical path length of the reference light.

Further, recently, as a system of rapidly obtaining a tomographic image without changing the optical path length of the reference light, there has been proposed an SD-OCT system using SD-OCT (spectral domain OCT) measurement. In the SD-OCT measurement, a tomographic image is formed without scanning in the direction of depth, by dividing broadband, low coherence light from a light source into measuring light and reference light by the use of a Michelson interferometer, causing the reflected light returning from the object when the measuring light is projected onto the object to interfere with the reference light and carrying out Fourier analysis on each channeled spectrum obtained by decomposing the interference light of the reflected light and the reference light into frequency components.

Whereas, as a further system for rapidly obtaining a tomographic image without changing the optical path length of the reference light, there has been proposed a system using SS-OCT (swept source OCT) measurement. In the SS-OCT system, a tomographic image is obtained on the basis of an intensity of reflected light in a position in the direction of depth of the object by sweeping the frequency of the laser beam emitted from the light source to cause the reflected light and the reference light to interfere with each other at various wavelengths and carrying out a Fourier analysis on the interference spectrum for a series of wavelengths to obtain the intensity of the reflected light in the position in the direction of depth of the object.

When each of the optical tomography systems described above is applied to an endoscope, a laser is generally used as the light source and an optical fiber is generally employed to guide light to a body cavity. Accordingly, problems related to polarization arises as follows.

Because they have polarization characteristics, the optical parts used in the above systems exhibit different transmissivities, reflectances, branching ratios and the like depending on the direction in which the incident light is polarized. Especially, when the light incident to the optical parts substantially comprises only linearly polarized light polarized in one direction, the influence of the polarization characteristics appears large. When the direction of polarization of the incident light changes, the influence of the polarization is enlarged.

An optical fiber is necessarily folded or twisted when it is inserted into a body cavity. Further, temperature changes of the fiber inherent to insertion into a body cavity occur. In a single-mode fiber which is generally used for an endoscope, the direction of polarization of light propagating through the fiber cannot be preserved. Accordingly, the state of polarization of light propagating through the fiber changes due to stress by folding or twisting, changing factors such as a temperature change or vibration. That is, light propagating through the fiber constantly fluctuates in its state of polarization.

When light which fluctuates in its state of polarization impinges upon the optical parts, the signal level to be detected by a detector by way of the optical parts fluctuates, S/N ratio deteriorates, and values different from the inherent measured values can be obtained. As a result, the quality of the tomographic image can deteriorate, for instance, the tomographic image can be rough and those which is to be distinguished cannot be distinguished from each other. Thus, the change in the image quality due to fluctuation in the state of polarization is especially enlarged when the light is linearly polarized light.

When the reflected light from the object and the reference light are both perfectly linearly polarized, and the directions of polarization are perpendicular to each other, there arises an event where no interference can take place and no tomographic image can be obtained. On the other hand, when each of the reflected light and the reference light is elliptically or circularly polarized, since the interference components of each light perpendicular to each other cannot be nullified even if the state of polarization of each polarized light somewhat changes, and accordingly, an event where no interference can take place seldom occurs and the signal level only somewhat changes, whereby the influence is relatively small.

In Japanese Unexamined Patent Publication No. 2000-262461, there has been disclosed to use on the front end of the probe an element such as a Faraday rotator which rotates the plane of polarization by 45° in order to compensate for change of the interference light due to change of the refractive index caused by curving of the optical fiber and to use a polarization plane controller in order to maximize the interference intensity of the reflected light from the object with the reference light by equalizing directions of polarization of the reflected light and the reference light. However, in order to dispose a Faraday rotator on the front end of the thin probe which is to be inserted into a body cavity, it is necessary to miniaturize the Faraday rotor. The Faraday rotors which can be miniaturized are limited in their wavelength and are inadequate to the above optical tomography system. The polarization plane controller has drawbacks that it acts at low speed since it is mechanically driven, adds to the size of the system, are instable since it is high in the sensitivity and requires adjustment by a man each time the state of propagation in the fiber changes, and is not practical.

SUMMARY OF THE INVENTION

In view of the foregoing observations and description, the primary object of the present invention is to provide an optical tomography system in which the influence of the polarization is suppressed and a tomographic image which is excellent in the image quality can be obtained.

Another object of the present invention is to provide a method of adjusting quality of an image obtained by a tomography system.

In accordance with the present invention, there is provided an optical tomography system for obtaining a tomographic image of an object comprising a light source unit which emits light, a light dividing means which divides the light emitted from the light source unit into measuring light and reference light, a combining means which combines the reflected light from the object when the measuring light is projected onto the object and the reference light, an interference light detecting means which detects interference light of the reflected light and the reference light which have been combined by the combining means, and an image obtaining means which obtains a tomographic image of the object on the basis of the interference light detected by the interference light detecting means, wherein the improvement comprises that a polarization changing means which converts linearly polarized light to non-linearly polarized light is provided in at least one of the light source unit, the optical path from the light source unit to the light dividing means, the optical path of the measuring light from the light dividing means to the object, the optical path of the reflected light from the object to the combining means and the optical path of the reference light from the light dividing means to the combining means.

The "non-linearly polarized light" means, for instance, right circularly polarized light, left circularly polarized light, right elliptically polarized light, left elliptically polarized light, or non-polarized light.

In this case, the polarization changing means may comprise a polarization-preserving optical fiber which is disposed so that the direction of polarization of the linearly polarized light and the direction of axis of polarization of the linearly polarized light differ from each other.

The "axis of polarization" means an axis which is inherent to the polarization-preserving optical fiber and when the linearly polarized light impinges thereupon with the direction of polarization of the linearly polarized light conforming to the direction of the axis of polarization, the linearly polarized light can be propagated with the direction of polarization thereof preserved. When linearly polarized light the direction of polarization of which differs from the direction of the axis of polarization of the polarization-preserving optical fiber enters the polarization-preserving optical fiber, the state of polarization of the linearly polarized light is not preserved and changes with the propagation of the linearly polarized light and the linearly polarized light appears only when the propagating distance is a particular distance. That is, the emitted light is linearly polarized light only when the length of the polarization-preserving optical fiber is a particular length, and the emitted light is non-linearly polarized light when the length of the polarization-preserving optical fiber is a length other than the particular length. This invention structures the polarization changing means by the use of the above characteristics of the polarization-preserving optical fiber.

The polarization changing means may comprise at least two polarization-preserving optical fibers which are disposed to be different from each other in the direction of axis of polarization.

When the polarization-preserving optical fiber is used, it is preferred that the length of the polarization-preserving optical fiber be not an integer times a half of a beat length.

The "beat length" means a propagating length by which linearly polarized light travels before linearly polarized light polarized in a direction different from the direction of the axis of polarization of the polarization-preserving optical fiber becomes linearly polarized light polarized again in a direction the same as that when it enters the polarization-preserving optical fiber after propagation through the polarization-preserving optical fiber, and the "half of the beat length" means a propagating length by which linearly polarized light travels before linearly polarized light polarized in a direction different from the direction of the axis of polarization of the polarization-preserving optical fiber becomes linearly polarized light polarized in a direction perpendicular to that when it enters the polarization-preserving optical fiber after propagation through the polarization-preserving optical fiber.

At least one of the polarization-preserving optical fibers is rotatable about the optical axis and a control means which controls the rotating angle of the rotatable polarization-preserving optical fiber according to the result of the detection by the interference light detecting means may be further provided.

Further, the polarization changing means may comprise either a wavelength plate or a polarization releasing plate.

The "wavelength plate" is a birefringent element which when linearly polarized lights which oscillate in directions perpendicular to each other pass the board, gives a predetermined phase difference to these lights and has an inherent axis of polarization.

Only when the direction of polarization of incident linearly polarized light is at a predetermined angle to the axis of polarization of the wavelength plate, the emitted light is linearly polarized, and when the direction of polarization of incident linearly polarized light is at other angles to the axis of polarization of the wavelength plate, the emitted light is non-linearly-polarized. The present invention structures the polarization changing means by the use of the characteristics of the wavelength plate. The wavelength plate may be, for instance, a $1/4\lambda$ plate which gives a phase difference of $\pi/2$. Only when the direction of polarization of incident linearly polarized light is at 0° or 180° to the axis of polarization of the plate, the emitted light is linearly polarized. However, when the direction of polarization of incident linearly polarized light is at other angles to the axis of polarization of the $1/4\lambda$ plate, the emitted light is circularly or elliptically polarized.

The "polarization releasing plate" is an element which makes the emitted light non-polarized irrespective of the state of polarization of the incident light.

Further, the polarization changing means may comprise at least two wavelength plates which are disposed to be different from each other in the direction of axis of polarization.

At least one of the wavelength plates may be rotatable about the optical axis and a control means which controls the rotating angle of the rotatable wavelength plate according to the result of the detection by the interference light detecting means may be further provided.

The tomography system in accordance with the present invention may be a system using an SS-OCT measurement where the light source unit emits laser light which has been periodically swept the wavelength thereof, and the image obtaining means obtains a tomographic image of the object by frequency analysis of the interference light.

The tomography system in accordance with the present invention may be a system using an SD-OCT measurement where the light source unit emits low coherence light, and the image obtaining means obtains a tomographic image of the object by frequency analysis of the interference light.

In accordance with the present invention, there is further provided a first method of adjusting quality of an image obtained by an optical tomography system for obtaining a tomographic image of an object comprising a light source unit which emits light, a light dividing means which divides the light emitted from the light source unit into measuring light and reference light, a combining means which combines the reflected light from the object when the measuring light is projected onto the object and the reference light, an interference light detecting means which detects interference light of the reflected light and the reference light which have been combined by the combining means, an image obtaining means which obtains a tomographic image of the object on the basis of the interference light detected by the interference light detecting means, and at least one polarization-preserving optical fiber which converts linearly polarized light to non-linearly polarized light and is provided in at least one of the light source unit, the optical path from the light source unit to the light dividing means, the optical path of the measuring light from the light dividing means to the object, the optical path of the reflected light from the object to the combining means and the optical path of the reference light from the light dividing means to the combining means to be rotatable about the optical axis, characterized by the step of, when the tomographic image of the object is obtained from the interference light detected by the interference light detecting means, changing the rotating angle of the polarization-preserving optical fiber, whereby the quality of the tomographic image to be obtained is changed.

In accordance with the present invention, there is further provided a second method of adjusting quality of an image obtained by an optical tomography system for obtaining a tomographic image of an object comprising a light source unit which emits light, a light dividing means which divides the light emitted from the light source unit into measuring light and reference light, a combining means which combines the reflected light from the object when the measuring light is projected onto the object and the reference light, an interference light detecting means which detects interference light of the reflected light and the reference light which have been combined by the combining means, an image obtaining means which obtains a tomographic image of the object on the basis of the interference light detected by the interference light detecting means, and at least one wavelength plate which converts linearly polarized light to non-linearly polarized light and is provided in at least one of the light source unit, the optical path from the light source unit to the light dividing means, the optical path of the measuring light from the light dividing means to the object, the optical path of the reflected light from the object to the combining means and the optical path of the reference light from the light dividing means to the combining means to be rotatable about the optical axis, characterized by the step of, when the tomographic image of the object is obtained from the interference light detected by the interference light detecting means, changing the rotating angle of the wavelength plate, whereby the quality of the tomographic image to be obtained is changed.

In the tomography system in accordance with the present invention, since the polarization changing means which changes linearly polarized light to non-linearly polarized light is provided, the influence of the polarization characteristics can be suppressed. Accordingly, fluctuation in signal level which has been conventionally generated due to fluctuation in the state of polarization can be reduced and the S/N ratio can be improved, whereby a tomographic image of good quality can be obtained. Since the influence of the fluctuation in the state of polarization can be reduced, reproducibility can be improved with respect to repeated measurements or measurements on different dates. Since the probability that the light once converted to the non-linearly polarized light by the polarization changing means returns to perfect linearly polarized light is very weak, the case where the reflected light and the reference light become perfect linearly polarized lights which are perpendicular to each other in the direction of polarization can be avoided, and a tomographic image can be surely obtained.

When the polarization changing means comprises a polarization-preserving optical fiber which is disposed so that the direction of polarization of the linearly polarized light and the direction of axis of polarization of the linearly polarized light differ from each other, the polarization-preserving optical fiber can double the waveguide means and the polarization changing means, whereby the system can be simplified.

Further, when the polarization changing means comprises at least two polarization-preserving optical fibers which are disposed to be different from each other in the direction of axis of polarization, the emitted light can be more simply non-linearly polarized light since the emitted light is linearly polarized light only when the polarization-preserving optical fibers are all in a particular length as described above. Further, in this case, alignment of the direction of polarization of the incident light and the axis of polarization of the polarization-preserving optical fiber is unnecessary since an optical fiber having an axis of polarization in a direction different from the direction in which the linearly polarized light is polarized can be necessarily found without the direction of polarization of the incident light taken into a special account.

Further, when the length of the polarization-preserving optical fiber is not an integer times a half of a beat length, the direction of polarization of the emitted light can be necessarily different from the direction of polarization of the incident linearly polarized light and from a direction perpendicular thereto.

When at least one of the polarization-preserving optical fibers is rotatable about the optical axis and a control means which controls the rotating angle of the rotatable polarization-preserving optical fiber according to the result of the detection by the interference light detecting means is further provided, the state of polarization of light emitted from the polarization changing means is changed by changing the rotating angle of the rotatable polarization-preserving optical fiber and the quality of the tomographic image obtained is changed with the change of the state of polarization of the light emitted from the polarization changing means. Accordingly, the quality of the tomographic image obtained can be adjusted by changing the rotating angle of the rotatable polarization-preserving optical fiber so that an optimal quality can be obtained.

When a wavelength plate is used as the polarization changing means, the polarization changing means can be realized in a simple structure.

When the polarization changing means comprises at least two wavelength plates which are disposed to be different from each other in the direction of axis of polarization, the emitted light can be more easily non-polarized light since the emitted light is linearly polarized only when the axis of polarization of all the wavelength plates is at a predetermined angle to the direction of polarization of incident linearly polarized light as described above.

When at least one of the wavelength plates is rotatable about the optical axis and a control means which controls the rotating angle of the rotatable wavelength plate according to the result of the detection by the interference light detecting means is further provided, the state of polarization of light emitted from the polarization changing means is changed by changing the rotating angle of the rotatable wavelength plate and the quality of the tomographic image obtained is changed with the change of the state of polarization of the light emitted from the polarization changing means. Accordingly, the quality of the tomographic image obtained can be adjusted by changing the rotating angle of the rotatable wavelength plate so that an optimal quality can be obtained.

When a polarization releasing plate is used as the polarization changing means, the polarization changing means can be realized in a simple structure. Further, since the emitted light is non-polarized in this case, influence of polarization characteristics hardly appears and a problem of fluctuation in the state of polarization can be overcome, whereby an excellent quality of tomographic image can be obtained. Further, since the polarization releasing plate is an element which makes the emitted light non-polarized irrespective of the state of polarization of the incident light, alignment such as a combination of the axes taking into account the direction of polarization of the incident light is unnecessary.

When the light source unit emits laser light which has been periodically swept the wavelength thereof, and the image obtaining means obtains a tomographic image of the object by frequency analysis of the interference light, the tomography system in accordance with the present invention may be a system using an SS-OCT measurement, and an optical tomographic image can be obtained at high speed without changing the optical path length of the reference light.

Further, in accordance with the first method of adjusting quality of a tomographic image obtained by an optical tomography system, an optical tomographic image of a best quality can be obtained by setting the rotating angle of the polarization-preserving fiber at which an optical tomographic image of a best quality can be obtained according to the condition at that time, since the rotating angle of the polarization-preserving fiber is changed, thereby changing the state of polarization of the emitted light, and the optical tomographic image is obtained viewing the quality of the tomographic image which changes with the state of polarization of the emitted light.

Further, in accordance with the second method of adjusting quality of a tomographic image obtained by an optical tomography system, an optical tomographic image of a best quality can be obtained by setting the rotating angle of the wavelength plate at which an optical tomographic image of a best quality can be obtained according to the condition at that time, since the rotating angle of the wavelength plate is changed, thereby changing the state of polarization of the emitted light, and the optical tomographic image is obtained viewing the quality of the tomographic image which changes with the state of polarization of the emitted light.

DESCRIPTION OF THE PREFERRED EMBODIMENTS

Embodiments of the optical tomography system of the present invention will be described in detail with reference to the drawings, hereinbelow.

Figure 1:
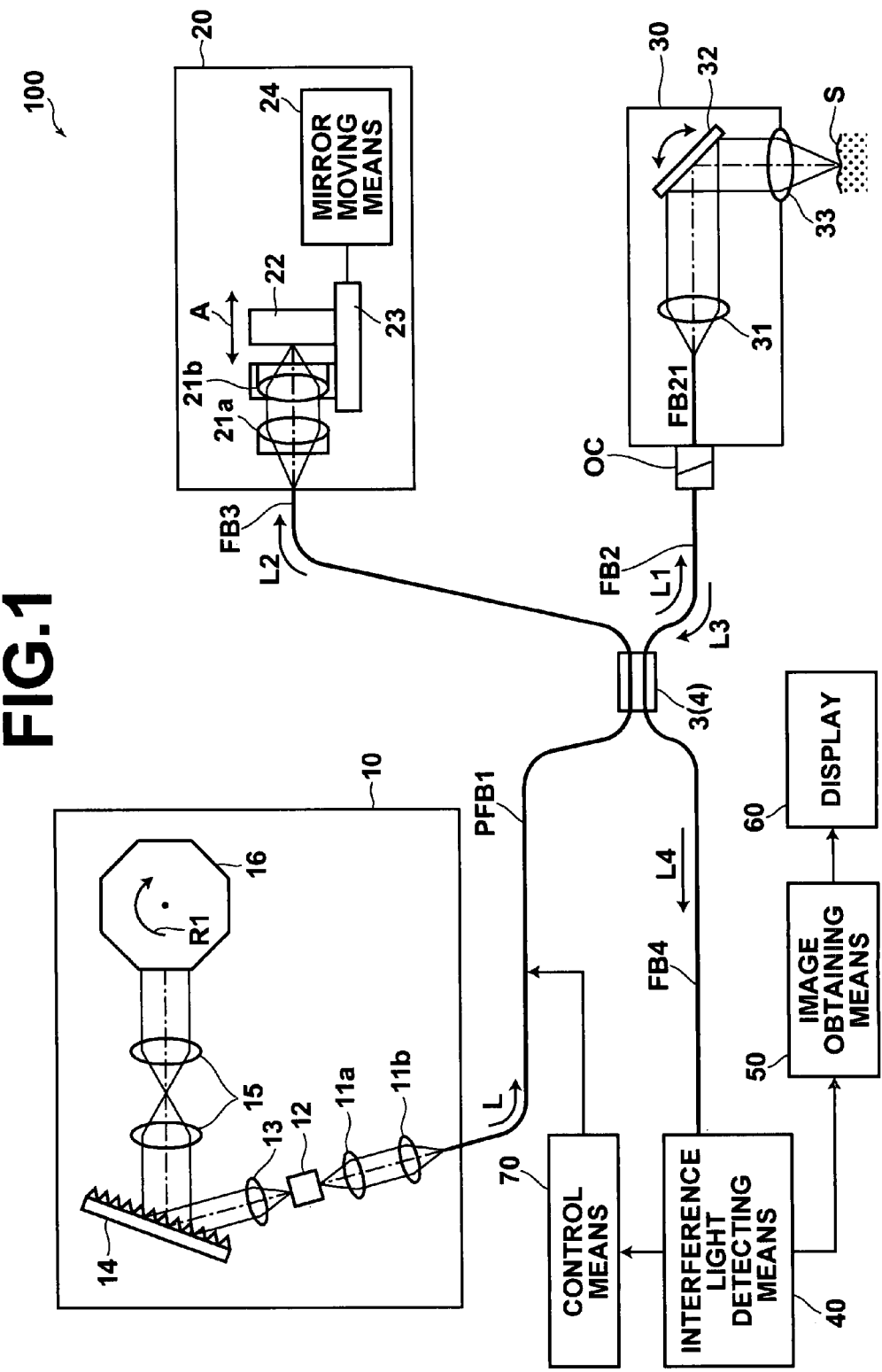
FIG. 1 is a view showing an optical tomography system in accordance with a first embodiment of the present invention.

FIG. 1 is a view that illustrates an optical tomography system in accordance with a first embodiment of the present invention. The optical tomography system 100 of this embodiment is for obtaining a tomographic image of an object of measurement such as a living tissue or a cell in a body cavity by measuring the SD-OCT. The optical tomography system 100 of this embodiment comprises: a light source unit 10 which emits light L; a light dividing means 3 which divides the light L emitted from the light source unit 10 into measuring light beam L1 and reference light beam L2; an optical path length adjusting means 20 which adjusts the optical path length of the reference light beam L2 divided by the light dividing means; a probe 30 which guides to the object S to be measured the measuring light beam L1 divided by the light dividing means 3; a combining means 4 for combining a reflected light beam L3 from the object S when the measuring light beam L1 is irradiated onto the object S from the probe 30, and the reference light beam L2; an interference light detecting means 40 for detecting interference light beam L4 of the reflected light beam L3 and the reference light beam L2 which have been combined by the combining means 4; and an image obtaining means 50 which obtains a tomographic image of the object S by carrying out frequency-analysis on the interference light L4 detected by the interference light detecting means 40.

The light source unit 10 emits laser light L which is periodically swept the wavelength thereof, and as a laser medium, a semiconductor laser medium which is used in semiconductor laser is employed. Specifically, the light source unit 10 comprises a pair of a light coupling lenses 11a and 11b, a semiconductor laser medium 12, collimating lens 13, a diffractive optics 14, a relay lens 15 and a polygon mirror 16.

Light emitted from the semiconductor laser medium 12 is turned to parallel light by the collimating lens 13, spatially dispersed by the wavelengths by the diffractive optics 14, and is reflected by the polygon mirror 16 by way of the relay lens 15. A part of the reflected light travels the reverse optical path and returns to the semiconductor laser medium 12 as return light.

The rotating polygon mirror 16 rotates in the direction indicated by arrow R1, to vary the angle of each reflective surface thereof with respect to the optical axis of the relay lens 15. Thereby, only a light beam having a specific frequency, from among the light spectrally split by the diffractive optics 14, is returned to the semiconductor laser medium 12 as the return light. A resonator is formed by the light emitting end face of the semiconductor laser medium 12 facing the collimating lens 13 and the polygon mirror 16, and laser light L is emitted from the light emitting end face of the semiconductor laser medium 12 facing the light coupling lens 11a. The wavelength of the laser light L is the wavelength of the return light. Laser light L emitted from the semiconductor laser medium 12 is turned to parallel light by the lens 11a and collected by the lens 11b to enter an optical fiber PFB1.

The wavelength of the return light is determined by the angle formed by the optical axis of the optical system 15 and the reflective surface of the rotating polygon mirror 16. Accordingly, when the rotating polygon mirror 16 rotates in the direction indicated by arrow R1 at a constant speed, the wavelength of the light beam which reenters the semiconductor laser medium 12 from the polygon mirror 16 changes at a period with time. As a result, a laser beam L which is swept in its wavelength at a period is emitted from the light source unit 10 toward the optical fiber PFB1. The laser light L enters the optical fiber PFB1 substantially in a state of linearly polarized light.

The optical fiber PFB1 is a polarization-preserving optical fiber and functions as a waveguide means and as the polarization changing means in the present invention. The optical fiber PFB1 has an inherent axis of polarization and is disposed so that the direction of the axis of polarization differs from the direction of linear polarization of the laser light L.

Figure 2:
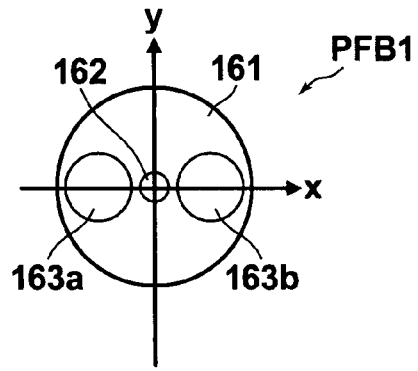
FIG. 2 is a cross-sectional view of the PANDA fiber.

FIG. 2 shows in cross-section, as an example of the polarization-preserving optical fiber, a PANDA (polarization-maintaining and absorption-reducing) fiber. As shown in FIG. 2, the PANDA fiber is provided with a pair of non-axial-symmetric stresses giving stressing portions 163a and 163b on opposite sides of the core 162 centrally disposed in a clad 161. The direction parallel to the direction in which the stressing portions 163a and 163b are arranged is the x-axis while the direction perpendicular thereto is the y-axis.

Figure 3:
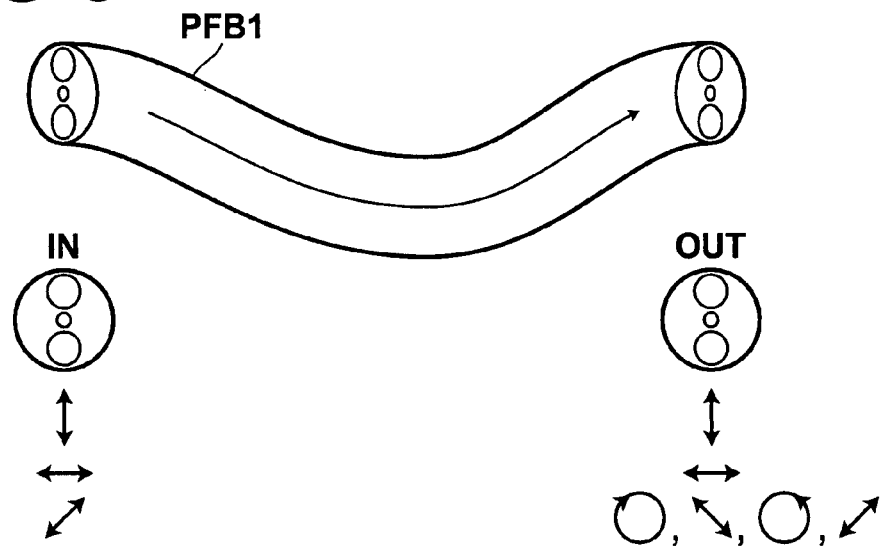
FIG. 3 is a view for illustrating the states of polarization of incident light and emitted light to and from the polarization-preserving fiber.

The states of polarization of light entering the polarization-preserving optical fiber ("IN side") and the state of polarization of light emitted from the polarization-preserving optical fiber when the light in each state of polarization propagates the polarization-preserving optical fiber and is emitted therefrom ("OUT side") are schematically shown by the arrows in FIG. 3. In FIG. 3, a pair of linearly polarized lights which are polarized in the same direction as the axes of polarization and linearly polarized light which is polarized in a direction different from the axis of polarization are shown. As can be understood from FIG. 3, when linearly polarized light polarized in the same direction as the axis of polarization enters a polarization-preserving optical fiber, the linearly polarized light is guided with the direction of polarization preserved. However, when linearly polarized light polarized in a direction different from the axis of polarization enters a polarization-preserving optical fiber, the direction of polarization of the linearly polarized light is not preserved and changes with propagation of the linearly polarized light so that the state of polarization of the light to be emitted is changed according to the propagating distance and right circularly polarized light, left circularly polarized light, and linearly polarized light polarized in a direction different from the direction in which the light is polarized when entering the polarization-preserving optical fiber can appear.

Figure 4:
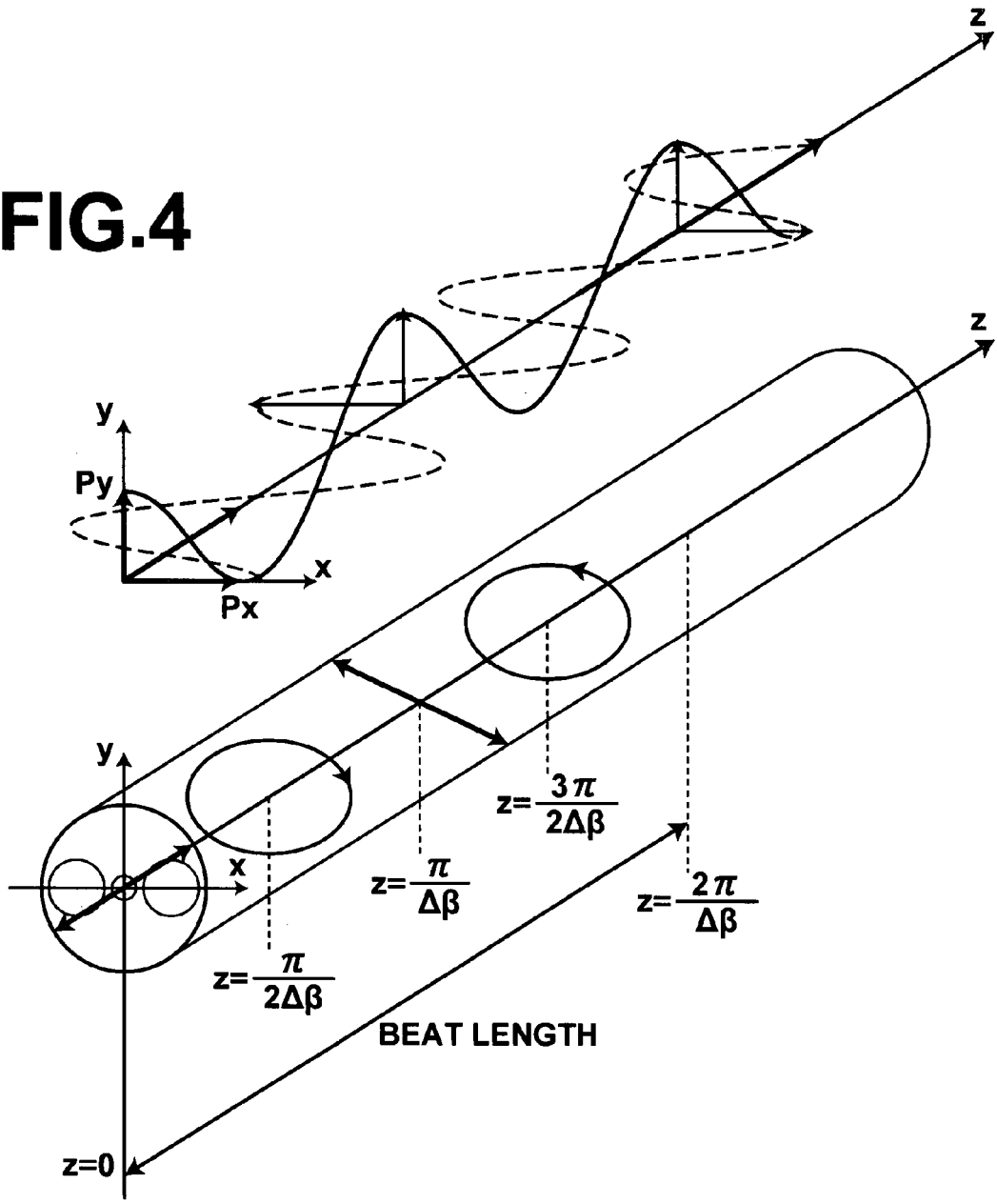
FIG. 4 is a schematic view showing change in travel of light and the state of polarization of light when polarized light polarized in a direction at 54° to the axis of polarization of the polarization-preserving fiber enters the polarization-preserving fiber.

Change in propagation of light and in the state of polarization of light when linearly polarized light impinges upon a polarization-preserving optical fiber at 45o to the axis of polarization thereof are shown in more detail in FIG. 4. In FIG. 4, the x-, and the y-axis direction components of the incident linearly polarized light are respectively represented by Px and Py and the direction perpendicular to the x-axis and y-axis shown in FIG. 2 is denoted as the direction of z-axis, the direction of propagation of light. As shown in FIG. 4, the state of polarization of light propagating through the polarization-preserving optical fiber changes according to the propagating distance. When it is assumed that the difference between the propagation constants in the directions of the x-axis and the y-axis is $\Delta\beta$, the light is circularly polarized when the propagating distance is $\pi/2\Delta\beta$ and $3\pi/2\Delta\beta$ while is linearly polarized in a direction perpendicular to the direction in which the light is polarized when entering the polarization-preserving optical fiber when the propagating distance is $\pi/\Delta\beta$ and is linearly polarized in the same direction as the direction in which the light is polarized when entering the polarization-preserving optical fiber when the propagating distance is $2\pi/\Delta\beta$. The length of $2\pi/\Delta\beta$ is referred to as the "beat length" and the length of the optical fiber PFB1 is not an integer times a beat length.

As can be seen from FIG. 4, when linearly polarized light the direction of polarization of which differs from the direction of the axis of polarization of the polarization-preserving optical fiber enters the polarization-preserving optical fiber, the emitted light is linearly polarized light only when the length of the polarization-preserving optical fiber is a particular length, and otherwise is non-linearly polarized light. Accordingly, when the angle which the axis of polarization makes to the direction of polarization of the polarized light, the difference $\Delta\beta$ between the propagation constants, and the length of the optical fiber PFB1 are taken into account, the emitted light can be non-linearly polarized light.

Since having a polarization characteristics, the optical parts such as the mirrors or the fiber couplers exhibit different transmissivities, reflectances, branching ratio and the like in the case of P-polarized light (linearly polarized light where the electric field oscillates in a plane parallel to the incident face of the linearly polarized light) and the S-polarized light (linearly polarized light where the electric field oscillates in a plane perpendicular to the incident face of the linearly polarized light). When the light incident to the optical parts comprises only linearly polarized light polarized in one direction, the influence of the polarization characteristics appears especially large. For example, when light incident to a mirror comprises linearly polarized light and comprises only P-polarized light, the amount of the reflected light depends upon the reflectance of the P-polarized light. On the other hand, when light incident to a mirror comprises circularly polarized light, since the circularly polarized light may be considered to comprise a pair of linearly polarized lights the direction of polarization of which are normal to each other, the amount of the reflected light depends upon the average of the reflectance to P-polarized light and the reflectance to S-polarized light. Further, when the state of polarization of incident light is changed and the direction of polarization of incident light changes by 90°, light which was originally P-polarized light turns to S-polarized light and the amount of the reflected light largely changes. On the other hand, in the case of circularly polarized light, the amount of the reflected light hardly changes even when the direction of polarization of incident light changes by 90°. This fact reveals that circularly polarized light is less sensitive to change of the state of polarization than linearly polarized light.

The optical fiber PFB1 is rotatable about the optical axis by an electric motor (not shown) and can be fixed at a desired rotating angle. By changing the rotating angle of the optical fiber PFB1, the angle which the axis of polarization of the optical fiber PFB1 makes to the direction of polarization of the polarized light incident to the optical fiber PFB1 can be changed and the state of polarization of light emitted from the optical fiber PFB1 can be changed, whereby the quality of the obtained tomographic image can be changed. The rotating angle of the optical fiber PFB1 is controlled by a control means 70. Otherwise, the direction of polarization of light entering the optical fiber PFB1 can be adjusted by inserting a ½λ plate between the lenses 11a and 11b and by rotating it in a plane perpendicular to the optical axis. The ½λ plate has a function of rotating the direction of polarization of light without changing the linearly polarized state of light. When the ½λ plate is rotated by angle θ, light whose direction of polarization is rotated by angle 2θ to the linearly polarized light incident thereto is emitted therefrom. The rotating angle of the ½λ plate may also be controlled by the control means 70. Though the PANDA fiber has been described by way of example in the above description and FIGS. 2 to 4, the polarization-preserving optical fiber need not be limited to the PANDA fiber but an ellipsoidal core fiber whose core is non-axial-symmetrical may be employed in this invention.

The light dividing means 3 of FIG. 1 comprises, for instance, a 2×2 fiber optic coupler and divides the laser beam L led thereto by way of the optical fiber PFB1 from the light source unit 10 into the measuring light beam L1 and the reference light beam L2. The light dividing means 3 is optically connected to two optical fibers FB2 and FB3, and the measuring light beam L1 is propagated through the optical fiber FB2 while the reference light beam L2 is propagated through the optical fiber FB3. The optical fibers FB2 and FB3 are both the single mode fiber. In this embodiment, the light dividing means 3 also functions as the combining means 4.

The probe 30 is optically connected to the optical fiber FB2 and the measuring light beam L1 is guided to the probe 30 from the optical fiber FB2. The probe 30 is inserted into a body cavity, for instance, through a forceps port by way of a forceps channel and is removably mounted on the optical fiber FB2 by an optical connector OC.

The optical probe 30 comprises: a single mode optical fiber FB21 which is provided inside a cylindrical probe outer envelope having a closed front end to extend in the direction of the axis of the outer envelope; a collimating lens 31 which makes parallel light L1 emitted from the front end of the optical fiber FB21, a scanning mirror 32 which reflects the measuring light L1 emitted from the collimating lens 31, and a collecting lens 33 which collects the measuring light L1 reflected by the scanning mirror 32 to converge on the object S. When the scanning mirror 32 is driven by a driving means (not shown), the object S can be scanned and can be measured.

An optical path length adjusting means 20 is disposed on the side of the optical fiber FB3 radiating the reference light beam L2. The optical path length adjusting means 20 changes the optical path length of the reference light beam L2 in order to adjust the position from which the tomographic image of the object S is initiated to be obtained and comprises a reflecting mirror 22 which reflects the reference light beam L2 radiated from the optical fiber FB3, a first lens 21a disposed between the reflecting mirror 22 and the optical fiber FB3, and a second lens 21b disposed between the first lens 21a and the reflecting mirror 22.

The first lens 21a makes parallel the reference light beam L2 radiated from the core of the optical fiber FB3 and at the same time, collects the reference light beam L2 reflected by the reflecting mirror 2 on the core of the optical fiber FB3. The second lens 21b collects the reference light beam L2 made parallel by the first lens 21a on the reflecting mirror 22 and at the same time, makes parallel the reference light beam L2 reflected by the reflecting mirror 22.

Accordingly, the reference light beam L2 radiated from the optical fiber FB3 is turned to a parallel light by the first lens 21a and is collected on the reflecting mirror 22 by the second lens 21b. Subsequently, the reference light beam L2 reflected by the reflecting mirror 22 is turned to a parallel light by the second lens 21b and is collected on the core of the optical fiber FB3 by the first lens 21a.

The optical path length adjusting means 20 is further provided with a movable stage 23 to which the second lens 21b and the reflecting mirror 22 are fixed and a mirror movement means 24 which moves the movable stage 23 in the direction of the optical axis of the first lens 21a. In response to movement of the movable stage 23 in the direction of arrow A, the optical path length of the reference light beam L2 can be changed.

The combining means 4 comprises a 2×2 fiber optic coupler as described above, and combines the reference light beam L2 which has been changed in its optical path length by the optical path length adjusting means 20 and the reflected light beam L3 from the object S to emit the interference light beam L4 toward the interference light detecting means 40 by way of an optical fiber FB4 which is the waveguide means. The optical fiber FB4 is a single mode optical fiber.

The interference light detecting means 40 detects the interference light L4 of the reflected light beam L3 and the reference light beam L2 which have been combined by the combining means. The interference light detecting means 40 is connected to the image obtaining means 50 comprising, for instance, a computer system such as a personal computer and the image obtaining means 50 is connected to a display system 60 formed, for instance, by a CRT or a liquid crystal display system. The image obtaining means 50 obtains reflection information in the position of depth by carrying out frequency analysis on the detected interference light beam L4. Then the image obtaining means 50 obtains a tomographic image on the basis of the intensity of the reflected light L3 in the direction of depth of the object S. The tomographic image is displayed by the displaying system 60. To the interference light detecting means 40, the control means 70 which controls the rotating angle of the optical fiber PFB1 on the basis of result of detection by the interference light detecting means 40 is further connected.

Here, detection of the interference light beam L4 in the interference light detecting means 40 and image generation in the image obtaining means 50 will be described briefly. Note that a detailed description of these points can be found in M. Takeda, "Optical Frequency Scanning Interference Microscopes", Optics Engineering Contact, Vol. 41, No. 7, pp. 426-432, 2003.

When the measuring light beam L1 is projected onto the object S, the reflected light L3 from each depth of the object S and the reference light L2 interfere with each other with various optical path length difference 1. When the light intensity of the interference fringe at this time versus each optical path length difference is assumed to be S(l), the light intensity I(k) detected in the interference light detecting means 40 is expressed by the following formula.

$$I(k) = \int_0^\infty S(l)[1+\cos(kl)]dl \tag{1}$$

wherein k represents the wave number and l represents the optical path length difference. Formula (1) may be considered to be given as an interferogram of an optical frequency range having a wave number k as a variable. Accordingly, a tomographic image can be generated by obtaining in the image obtaining means 50 reflection information in each position of depth of the object S by carrying out frequency analysis by Fourier-transform on the spectral interference light detected by the interference light detecting means 40 and determining the intensity S(l) of the interference light beam L4. The generated tomographic image is displayed by the displaying system 60.

Operation of the optical tomography system 100 having a structure described above will be described, hereinbelow. When a tomographic image is to be obtained, the optical path length is first adjusted by moving the movable stage 23 in the direction of the arrow A so that the object S is positioned in the measurable area. The light beam L is subsequently emitted from the light source unit 10 and the light beam L is divided into the measuring light beam L1 and the reference light beam L2 by the dividing means 3. The measuring light beam L1 is led by the optical probe 30 into a body cavity and is projected onto the object S. The reflected light beam L3 from the object S and the reference light beam L2 reflected by the reflecting mirror 22 are combined by the combining means 4, and the interference light beam L4 of the reflected light beam L3 and the reference light beam L2 is detected by the interference light detecting means 40. A tomographic image is obtained by carrying out frequency analysis on a signal of the detected interference light beam L4 in the image obtaining means 50. In the optical tomography system 100 where a tomographic image is obtained by measurement of SS-OCT, reflection information in each position of depth is obtained on the basis of the frequency and the intensity of the interference light beam L4 and movement of the reflecting mirror 22 in the direction of arrow A is employed to adjust the position in which a tomographic image is obtained.

By, for instance, driving the scanning mirror 32 so that the measuring light beam L1 scans the object S in the x-direction and the y-direction perpendicular to the x-direction, since information in each position of depth of the object S in the two-dimensional scanning area can be obtained, tomographic images of both the x-direction and the y-direction in the two-dimensional scanning area can be obtained.

When an optical tomographic image is to be obtained, the optical fiber PFB1 is rotated by the use of the control means 70 so that an optimal optical tomographic image is obtained. For example, the rotating angle of the optical fiber PFB1 may be fixed in a position where the optical tomographic image is optimal in the S/N ratio or the contrast. Such an adjustment may be effected not only during the measurement of the object S but also during assembly of the system or upon initiation of use of the system by preparing a standard sample. The adjustment of the image quality by the use of the control means 70 can also be done in the optical tomography systems in accordance with the following embodiments having a rotatable polarization changing means and the control means 70 for controlling the rotating angle of the rotatable polarization changing means.

In the optical tomography system 100, since linearly polarized light emitted from the light source unit 10 is converted to non-linearly polarized light by the use of an optical fiber PFB1, which is a polarization-preserving optical fiber, in the optical path from the light source unit 10 to the light dividing means 3, the influence of the optical parts on the polarization characteristics can be suppressed. Further, even if there is a fluctuation of the state of polarization in light propagating the optical fibers FB2, FB21, FB3 and FB4, which are a single mode fiber, the influence thereof is small. Accordingly, the fluctuation in the signal level is small and a tomographic image of an excellent quality can be obtained. Further, since the measurement is effected by the use of non-linearly polarized light, the reference light L2 and the reflected light L3 become perfect linearly polarized lights. Accordingly, the case where no optical tomographic image can be obtained can be avoided and a tomographic image can be surely obtained.

In the optical tomography system 100, since the optical fiber PFB1 can be rotated about the optical axis to a desired angle and fixed in the position, even if the state under which the system operates changes, a tomographic image of an excellent quality can be constantly obtained by adjusting the rotating angle of the optical fiber PFB1 by the control means 70 to an optimal angle according to the state.

Figure 5:
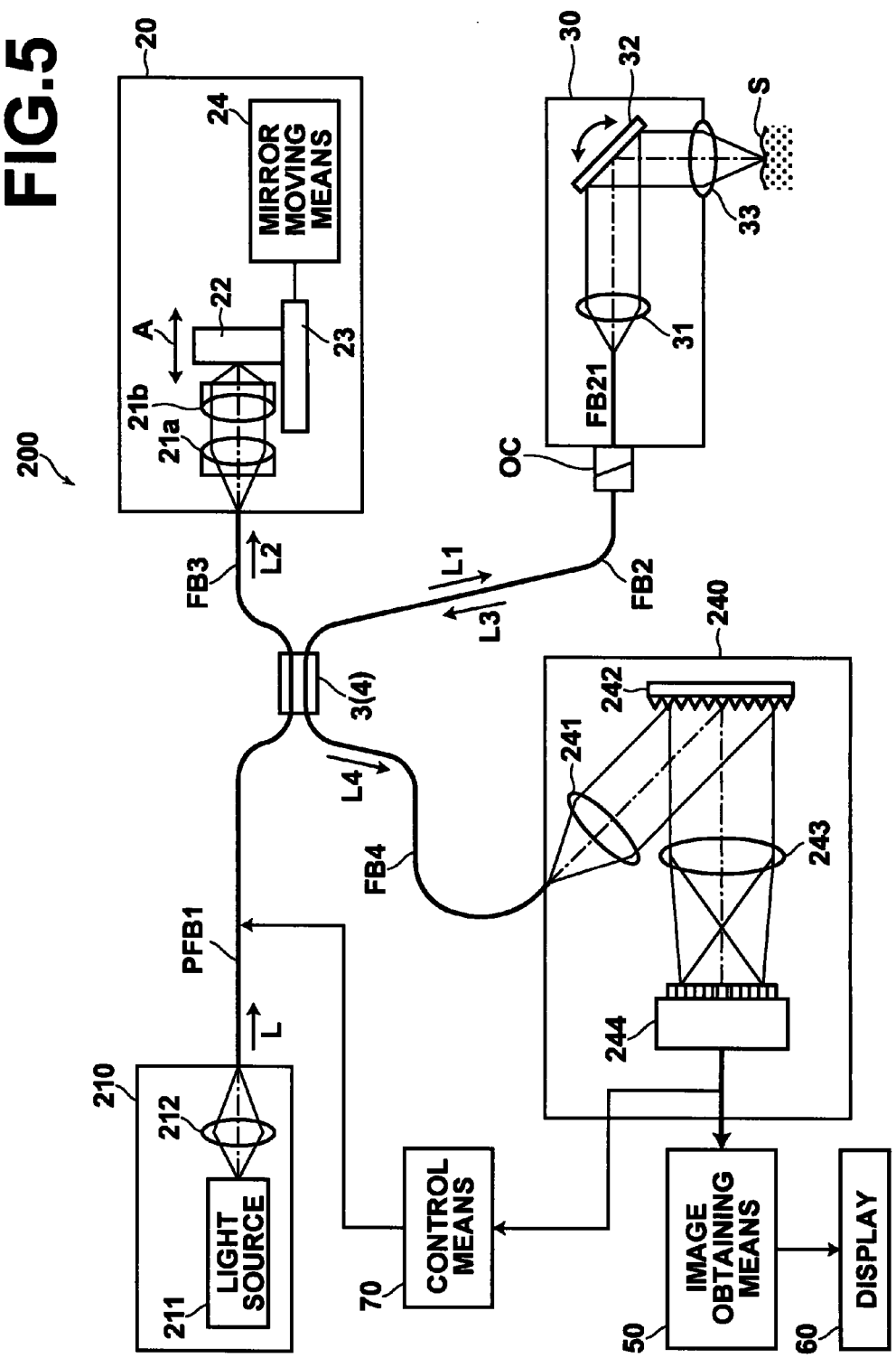
FIG. 5 is a view showing an optical tomography system in accordance with a second embodiment of the present invention.

An optical tomography system in accordance with a second embodiment of the present invention will be described with reference to FIG. 5, hereinbelow. Since the optical tomography system 200 in accordance with the second embodiment is a system which obtains a tomographic image by measurement of so-called an SD-OCT and differs from the embodiment shown FIG. 1 in a light source unit and interference light detecting means, in the optical tomography system 200 shown in FIG. 5, the elements analogous to those of the optical tomography system 100 shown in FIG. 1 are given the same reference numerals and description thereof will be abbreviated.

The light source unit 210 of the optical tomography system 200 comprises a light source 211 which emits low coherence light L such as an SLD (super luminescent diode), ASE (amplified spontaneous emission) and an optical system 212 which enters the light emitted from the light source 211 into an optical fiber PFB1. Since the optical tomography system 200 of this embodiment is for obtaining a tomographic image with a living tissue in a body cavity taken as the object S, it is preferred that the light source 11 be, for instance, a broad spectral band, ultra short pulse laser where attenuation of light due to scatter and/or absorption when transmitted through the object S is minimized.

An interference light detecting means 240 is for detecting the interference light L4 of the reflected light L3 and the reference light L2 which have been combined by the combining means 4, a spectral means 242 which spectrally divides by the wavelength band the interference light L4 with a plurality of wavelength bands which is entered from the polarization setting means 41, and the light detecting means 44 which are provided for each of the plurality of wavelength bands of the interference light L4 spectrally divided by the spectral means 242. The spectral means 242 comprises, for instance, a diffractive optics and spectrally divides the interference light L4 entering there from the optical fiber FB4 by way of a collimating lens 241 and emits the spectrally-divided light toward the light detecting means 244.

The light detecting means 244 has a plurality of, for instance, one-dimensionally or two-dimensionally arranged photosensors such as a CCD and each of the photosensors detects each wavelength band of the interference light beam L4 entering there by way of a lens 243. In the interference light detecting means 240, the interference light L4 where the spectrum of the light source unit 210 is added with a Fourier-transformed function of information on the reflection is observed. Then, by carrying out frequency analysis in the image obtaining means 50 on the interference light beam L4 detected in the interference light detecting means 240, reflection information in the position of depth can be obtained and a tomographic image is generated. The tomographic image is displayed by the displaying system 60.

Also in the optical tomography system 200 in accordance with the second embodiment, a polarization-preserving optical fiber is employed in the optical path from the light source unit 210 to the light dividing means 3. The optical fiber PFB1 in the optical tomography system 200 functions as the polarization changing means and disposed to be different in the direction of axis of polarization from the direction of polarization of the laser beam L which is emitted from the light source unit 210 and enters thereto. The length thereof is not an integer times a beat length and the optical fiber PFB1 is rotatable about the optical axis and its rotating angle is controlled by the control means 70.

In the optical tomography system 200 in accordance with the second embodiment described above, effects similar to those in the optical tomography system 100 in accordance with the first embodiment described above can be obtained and the influence of the polarization characteristics can be suppressed, whereby an optical tomographic image of an excellent quality can be obtained.

Figure 6:
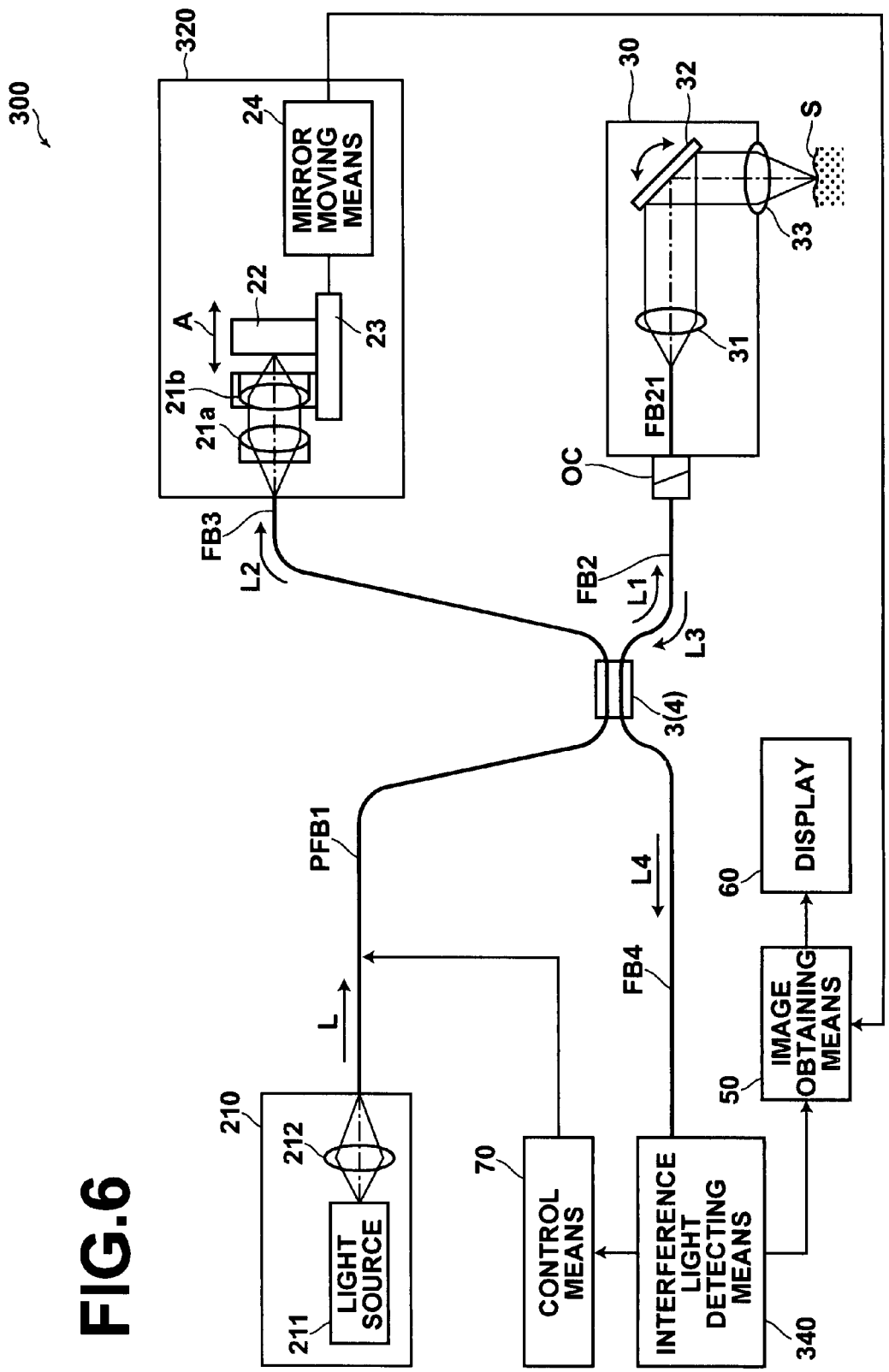
FIG. 6 is a view showing an optical tomography system in accordance with a third embodiment of the present invention.

An optical tomography system in accordance with a third embodiment of the present invention will be described with reference to FIG. 6, hereinbelow. Since the optical tomography system 300 in accordance with the third embodiment is a TD-OCT system where a tomographic image is obtained by TD-OCT measurement and differs from the first embodiment only in functions of the optical path length adjusting means and the interference light detecting means, the elements analogous to those in the tomography system 200 of FIG. 5 are given the same reference numerals and the description thereof is abbreviated in the tomography system 300 of FIG. 6.

Though having the structure similar to that 20 of the optical tomography system 100, the optical path length adjusting means 320 of the optical tomography system 300 has a function of changing optical path length of the reference light L2 in order to change the measuring position in the object S. Further, in the optical tomography system 300, a phase modulator 325 is disposed in the optical path of the reference light L2 (optical fiber FB3) to give a slight frequency shift to the reference light L2. The reference light L2 which has been changed in its optical path length and shifted in its frequency by the optical path length adjusting means 320 and the phase modulator 325 is guided to the combining means 4.

Interference light detecting means 340 detects by, for instance, heterodyne detection the intensity of the interference light L4. Specifically, when the sum of the total optical path length of the measuring light L1 and the total optical path length of the reflected light L3 is equal to the total optical path length of the reference light L2, a beat signal which varies in intensity at the difference frequency between the reference light L2 and the reflected light L3 is generated. As the optical path length is changed by the optical path length adjusting means 320, the measuring position (measuring depth) in the object S changes and the interference light detecting means 340 comes to detect a plurality of beat signals in the measuring positions. Information on the measuring position is output from the optical path length adjusting means 320 to the image obtaining means 50. On the basis of the beat signals detected by the interference light detecting means 340 and information on the measuring position in the mirror moving means 24, an optical tomographic image is generated by the image obtaining means 50. The generated optical tomographic image is displayed by the display system 60.

Also in the optical tomography system 300 in accordance with the third embodiment, a polarization-preserving optical fiber PFB1 is employed in the optical path from the light source unit 210 to the light dividing means 3. The optical fiber PFB1 in the optical tomography system 300 functions as the polarization changing means in the same manner as the optical fiber PFB1 in the optical tomography system 100 in accordance with the first embodiment and disposed to be different in the direction of axis of polarization from the direction of polarization of the laser beam L which is emitted from the light source unit 210 and enters thereto. The length thereof is not an integer times a beat length and the optical fiber PFB1 is rotatable about the optical axis and its rotating angle is controlled by the control means 70. In the third embodiment described above, effects similar to those in the optical tomography system 100 in accordance with the first embodiment described above can be obtained and the influence of the polarization characteristics can be suppressed, whereby an optical tomographic image of an excellent quality can be obtained.

Figure 7:
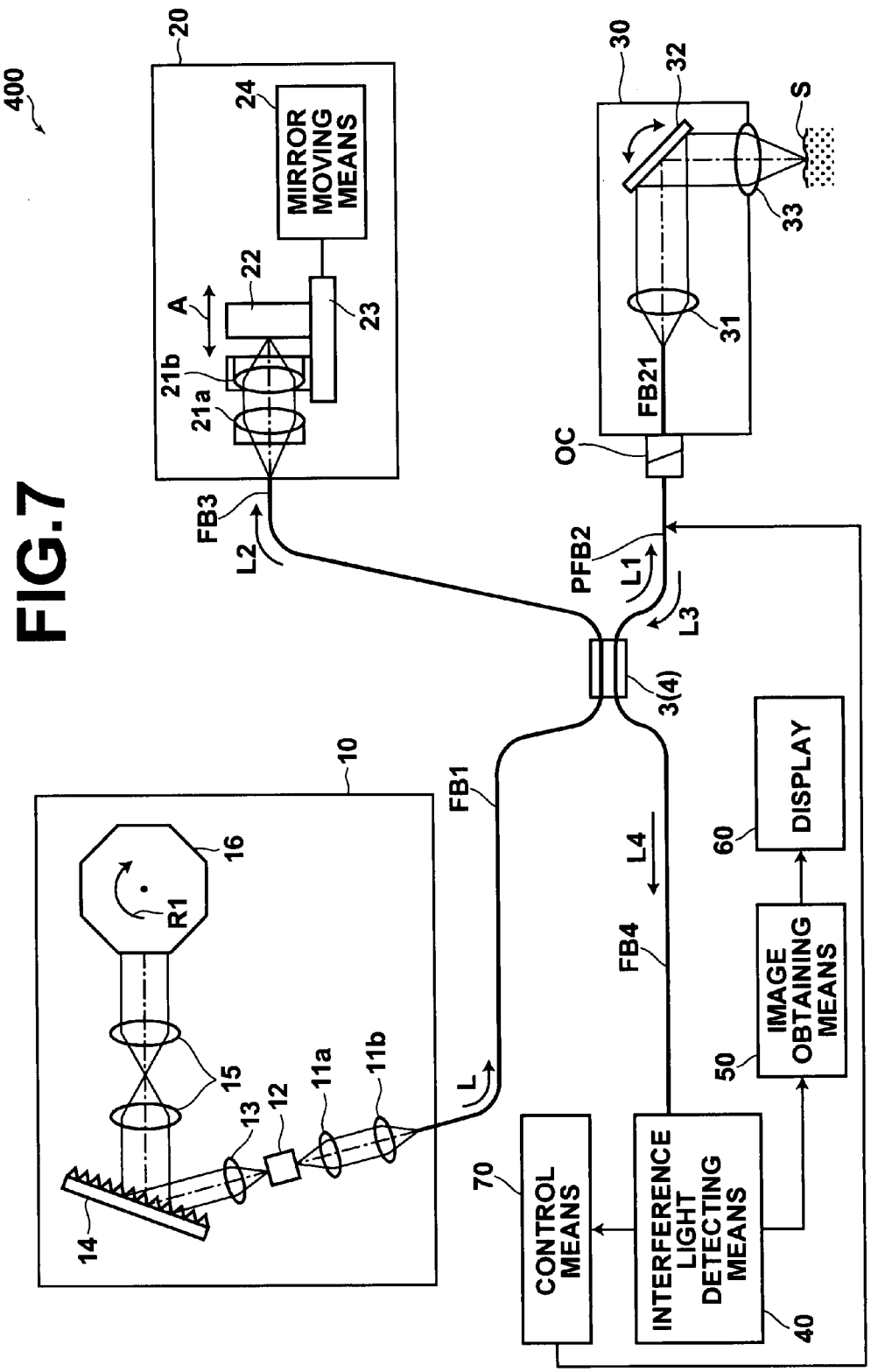
FIG. 7 is a view showing an optical tomography system in accordance with a fourth embodiment of the present invention.

An optical tomography system in accordance with a fourth embodiment of the present invention will be described with reference to FIG. 7, hereinbelow. Since the optical tomography system 400 in accordance with the fourth embodiment differs from the first embodiment only in that the polarization-preserving optical fiber is provided in the optical path of the measuring light L1 and the reflected light L3 instead of the optical path from the light source unit to the light dividing means, the elements analogous to those in the tomography system 100 of FIG. 1 are given the same reference numerals and the description thereof is abbreviated in the tomography system 400 of FIG. 7.

The optical tomography system 400 has a structure where a single mode fiber FB1 and a polarization-preserving optical fiber PFB2 are employed in place of the polarization-preserving optical fiber PFB1 and the single mode fiber FB2.

The optical fiber PFB2 which is the polarization-preserving optical fiber functions as the polarization changing means in the same manner as the optical fiber PFB1 in the optical tomography system 100 in accordance with the first embodiment and is disposed to be different in the direction of axis of polarization from the direction of polarization of the laser beam L which is emitted from the light source unit 210 and enters thereto. The length thereof is not an integer times a beat length and the optical fiber PFB1 is rotatable about the optical axis and its rotating angle is controlled by the control means 70.

In the optical tomography system 400 in accordance with the fourth embodiment described above, effects similar to those in the optical tomography system 100 in accordance with the first embodiment can be obtained and the influence of the polarization characteristics can be suppressed, whereby an optical tomographic image of an excellent quality can be obtained.

Figure 8:
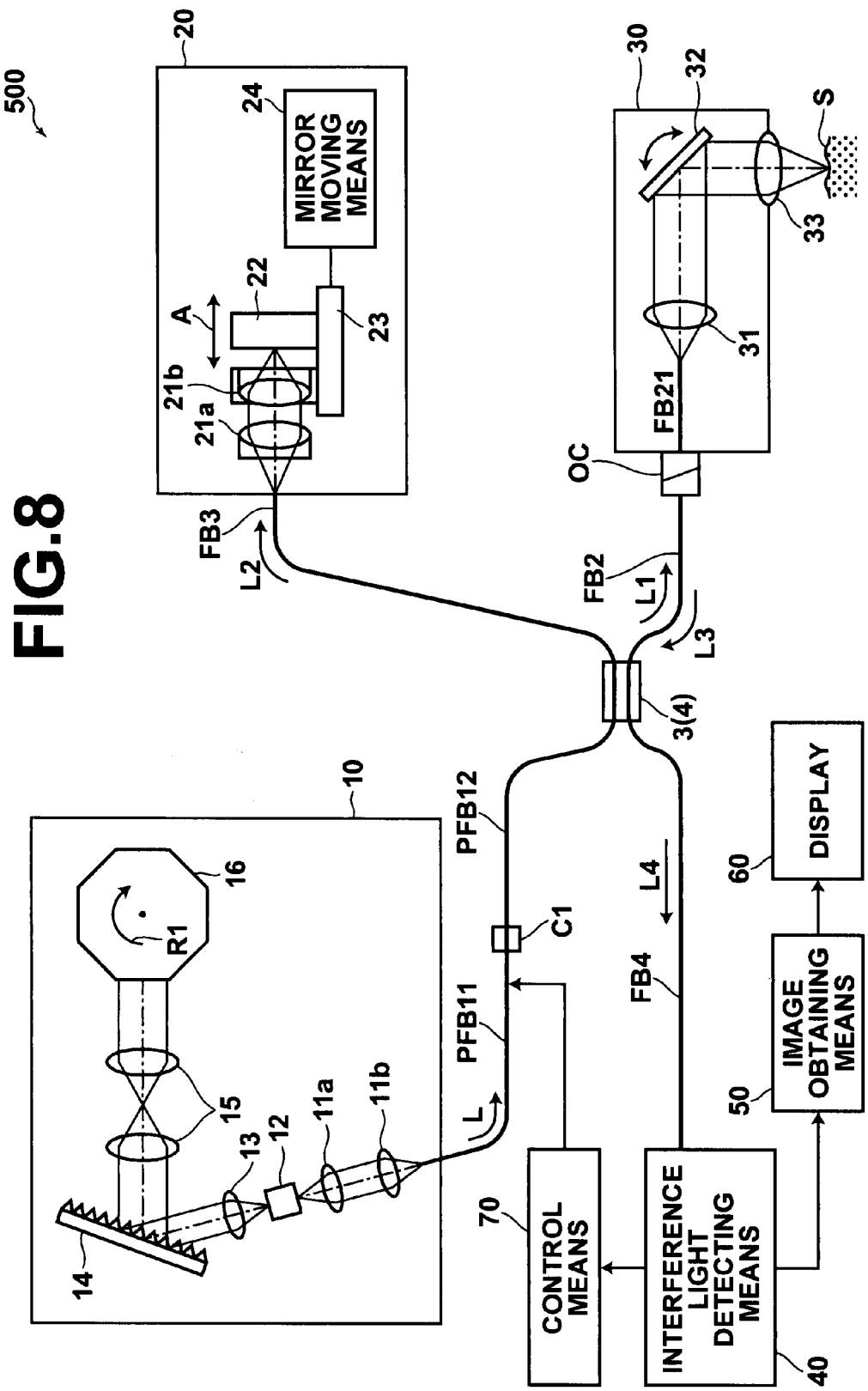
FIG. 8 is a view showing an optical tomography system in accordance with a fifth embodiment of the present invention.

An optical tomography system in accordance with a fifth embodiment of the present invention will be described with reference to FIG. 8, hereinbelow. Since the optical tomography system 500 in accordance with the fifth embodiment differs from the first embodiment only in that a pair of polarization-preserving optical fibers are provided, the elements analogous to those in the tomography system 100 of FIG. 1 are given the same reference numerals and the description thereof is abbreviated in the tomography system 500 of FIG. 8.

The optical tomography system 500 has a structure where a pair of polarization-preserving optical fibers PFB11 and PFB12 connected by an optical coupler C1 are employed in place of the polarization-preserving optical fiber PFB1 which is the polarization-preserving optical fiber in the optical tomography system 100 of FIG. 1.

Figure 9:
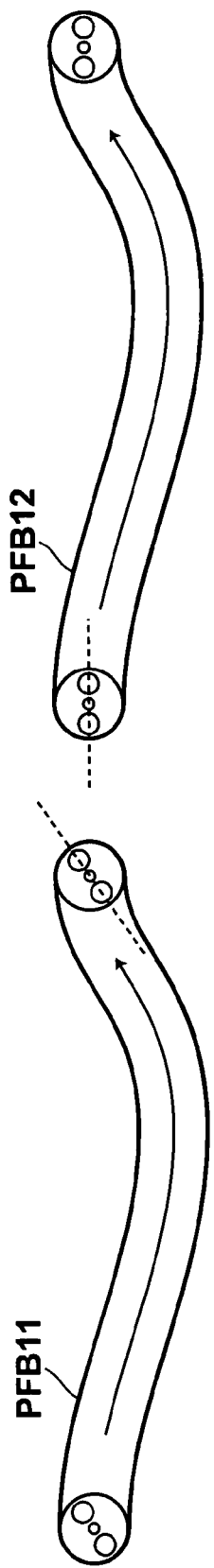
FIG. 9 is a view showing a pair of polarization-preserving fibers which are disposed to be different from each other in the axis of polarization.

The optical fibers PFB11 and PFB12 which are the polarization-preserving optical fibers function as the polarization changing means and are disposed in the junction thereof to be different from each other in the direction of axis of polarization as shown in FIG. 9. The lengths thereof are not an integer times a beat length. The optical fiber PFB11 is rotatable about the optical axis and its rotating angle is controlled by the control means 70. Though the optical coupler C1 which has no polarization-preserving function is employed in this particular embodiment, the optical coupler C1 which has a polarization-preserving function may be employed.

In the optical tomography system 500, the direction of polarization of linearly polarized light entering the optical fiber PFB11 from the light source unit 10 and the directions of the axis of polarization of the optical fibers PFB11 and PFB12 are not set. When the linearly polarized light impinges upon the optical fiber PFB11 with the direction of polarization of the linearly polarized light conforming to the direction of the axis of polarization of the optical fiber PFB11, linearly polarized light is emitted from the optical fiber PFB11 and the linearly polarized light enters the optical fiber PFB12. However, since the optical fibers PFB11 and PFB12 are disposed so that the directions of the axis of polarization of the optical fibers PFB11 and PFB12 are different from each other, the direction of polarization of linearly polarized light entering the optical fiber PFB12 differs from the axis of polarization of the optical fiber PFB12. Accordingly, in this case, light emitted from the optical fiber PFB12 may be non-linearly polarized as the light emitted from the optical fiber PFB1 in the first embodiment.

Further, when the direction of polarization of linearly polarized light emitting from the light source unit 10 differs from the direction of the axis of polarization of the optical fiber PFB11, light emitted from the optical fiber PFB11 may be non-linearly polarized as the light emitted from the optical fiber PFB1 in the first embodiment. When non-linearly polarized light enters the optical fiber PFB12, which is a polarization-preserving fiber, non-linearly polarized light is emitted from the optical fiber PFB12.

In the optical tomography system 500 in accordance with the fifth embodiment described above, effects similar to those in the optical tomography system 100 in accordance with the first embodiment can be obtained and the influence of the polarization characteristics can be suppressed, whereby an optical tomographic image of an excellent quality can be obtained. Further, when a pair of polarization-preserving optical fibers are used as in the fifth embodiment, the emitted light can be more simply non-linearly polarized light since the emitted light is linearly polarized light only when the polarization-preserving optical fibers are all in a particular length as described above. Further, in this case, alignment of the direction of polarization of the incident light and the axis of polarization of the polarization-preserving optical fiber is unnecessary in almost all the case since a polarization-preserving optical fiber having an axis of polarization in a direction different from the direction in which the linearly polarized light is polarized can be necessarily found without the direction of polarization of the incident light taken into a special account. However, the emitted light can be linearly polarized at a very weak probability according to the combination of the direction of polarization of incident light to the optical fiber PFB11 and the directions of the axis of polarization of the optical fibers PFB11 and PFB12. In such a case, by adjusting the direction of polarization of incident light to the optical fiber PFB11 or the angle which the axis of polarization of the optical fiber PFB11 makes to the axis of polarization of the optical fiber PFB12, the emitted light can be elliptically polarized.

Though one or two polarization-preserving fibers for functioning as the polarization changing means are provided in at least one of the optical path from the light source unit to the light dividing means and the optical path from the light dividing means to the probe in the first to fifth embodiments, the present invention need not be limited to such arrangements but the polarization-preserving fiber may be provided in at least one of the light source unit, the optical path from the light source unit to the light dividing means, the optical path from the light dividing means to the probe, the optical path from the optical connector OC in the probe to the object, and the optical path from the light dividing means to the combining means by way of the optical path length adjusting means, and may be provided at each of a plurality of places in these positions. When a polarization-preserving fiber is used as the polarization-preserving means, the polarization-preserving fiber need not form the whole optical path but may form only a part thereof.

An optical tomography system in accordance with a sixth embodiment of the present invention will be described with reference to FIG. 10, hereinbelow. The optical tomography system 600 in accordance with a sixth embodiment of the present invention is characterized in that a ¼λ plate is employed as the polarization changing means. Since the optical tomography system 600 in accordance with the sixth embodiment differs from the first embodiment only in that a single mode optical fiber FB1 is employed in place of the polarization-preserving optical fiber PFB1 and a light source 610 having a polarization changing means therein is employed in place of the light source unit 10, the elements analogous, to those in the tomography system 100 of FIG. 1 are given the same reference numerals and the description thereof is abbreviated in the tomography system 600 of FIG. 10.

The light source unit 610 of the tomography system 600 differs from the light source unit 10 of the tomography system 100 of FIG. 1 only in that a ¼λ plate 17 is disposed between the lenses 11a and 11b of the tomography system 100.

The ¼λ plate 17 is a birefringent plate which gives linearly polarized lights oscillating in directions perpendicular to each other a phase difference of the ¼ wavelength and functions as the polarization changing means in the present invention. The ¼λ plate 17 has an axis of polarization inherent thereto and emits linearly polarized light when the axis of polarization is at 0° or 180° to the direction of polarization of the incident linearly polarized light, while turns the incident linearly polarized light when the axis of polarization is at 45° to the direction of polarization of the incident linearly polarized light to circularly polarized light. When the axis of polarization is at the other angle to the direction of polarization of the incident linearly polarized light, the ¼λ plate 17 turns the incident linearly polarized light to elliptically polarized light.

The ¼λ plate 17 is rotatable about the optical axis by an electric motor (not shown). By changing the rotating angle of the ¼λ plate 17, the angle which the direction of polarization of linearly polarized light impinging upon the ¼λ plate 17 makes to the axis of polarization of the ¼λ plate 17 changes and the state of polarization of light emitted from the ¼λ plate 17 can be changed, whereby the quality of a tomographic image to be obtained can be changed. The rotating angle of the ¼λ plate 17 is controlled by the control means 70.

It is preferred that, when a tomographic image is to be obtained, the ¼λ plate 17 be rotated and fixed in a position where a good optical tomographic image is obtained by the use of the control means 70 as adjustment of rotation of the optical fiber PFB1 in the first embodiment.

In the optical tomography system 600 in accordance with the sixth embodiment described above, effects similar to those in the optical tomography system 100 in accordance with the first embodiment can be obtained and the influence of the polarization characteristics can be suppressed, whereby an optical tomographic image of an excellent quality can be obtained.

An optical tomography system in accordance with a seventh embodiment of the present invention will be described with reference to FIG. 11, hereinbelow. The optical tomography system 700 in accordance with a seventh embodiment of the present invention is characterized in that a ¼λ plate as the polarization changing means is added in the probe of the optical tomography system 600 of FIG. 10. Since the optical tomography system 700 in accordance with the seventh embodiment differs from the sixth embodiment only in that a ¼λ plate as the polarization changing means is added in the probe of the optical tomography system 600 of FIG. 10, the elements analogous to those in the tomography system 600 of FIG. 10 are given the same reference numerals and the description thereof is abbreviated in the tomography system 700 of FIG. 11.

Figure 10:
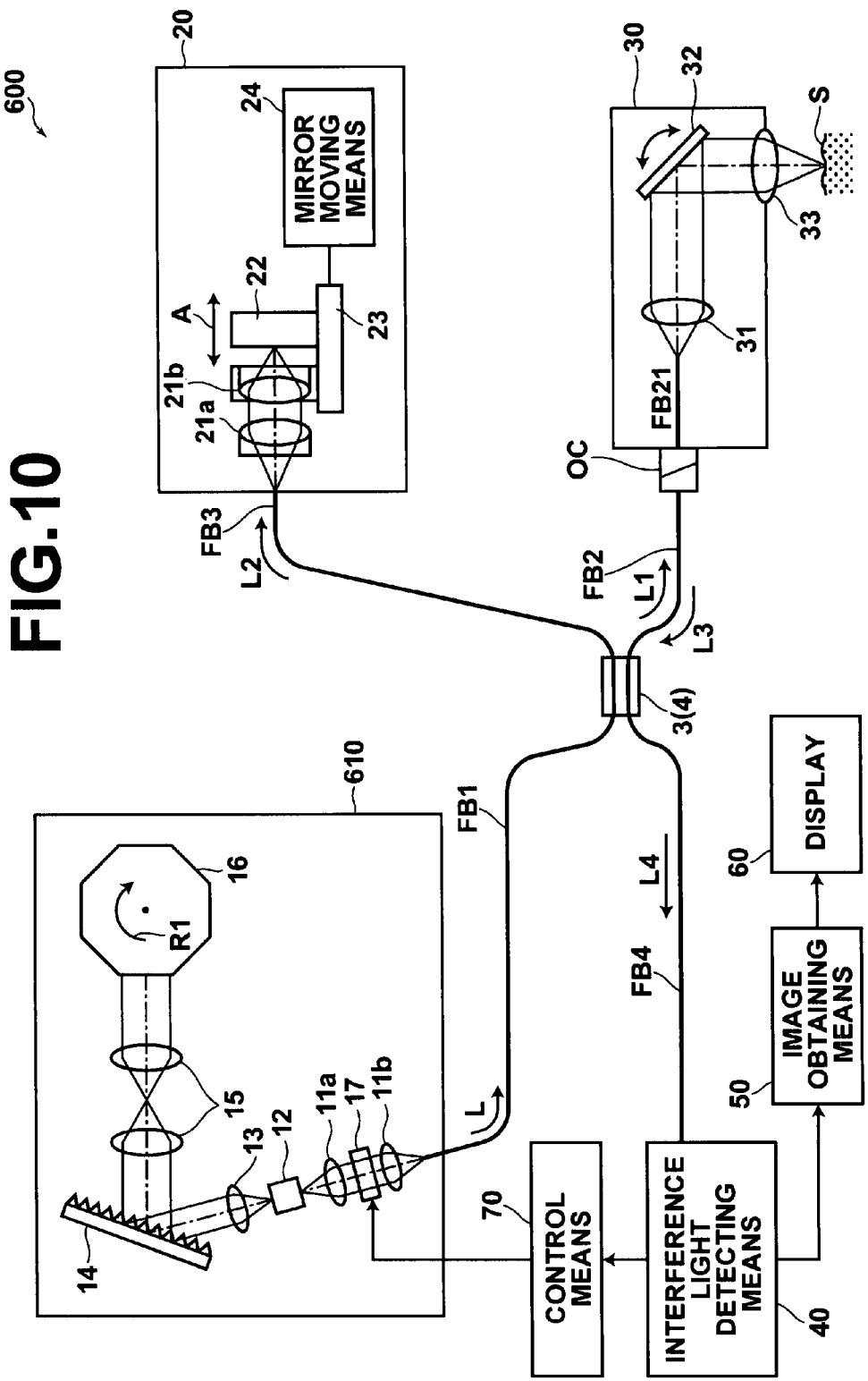
FIG. 10 is a view showing an optical tomography system in accordance with a sixth embodiment of the present invention.
Figure 11:
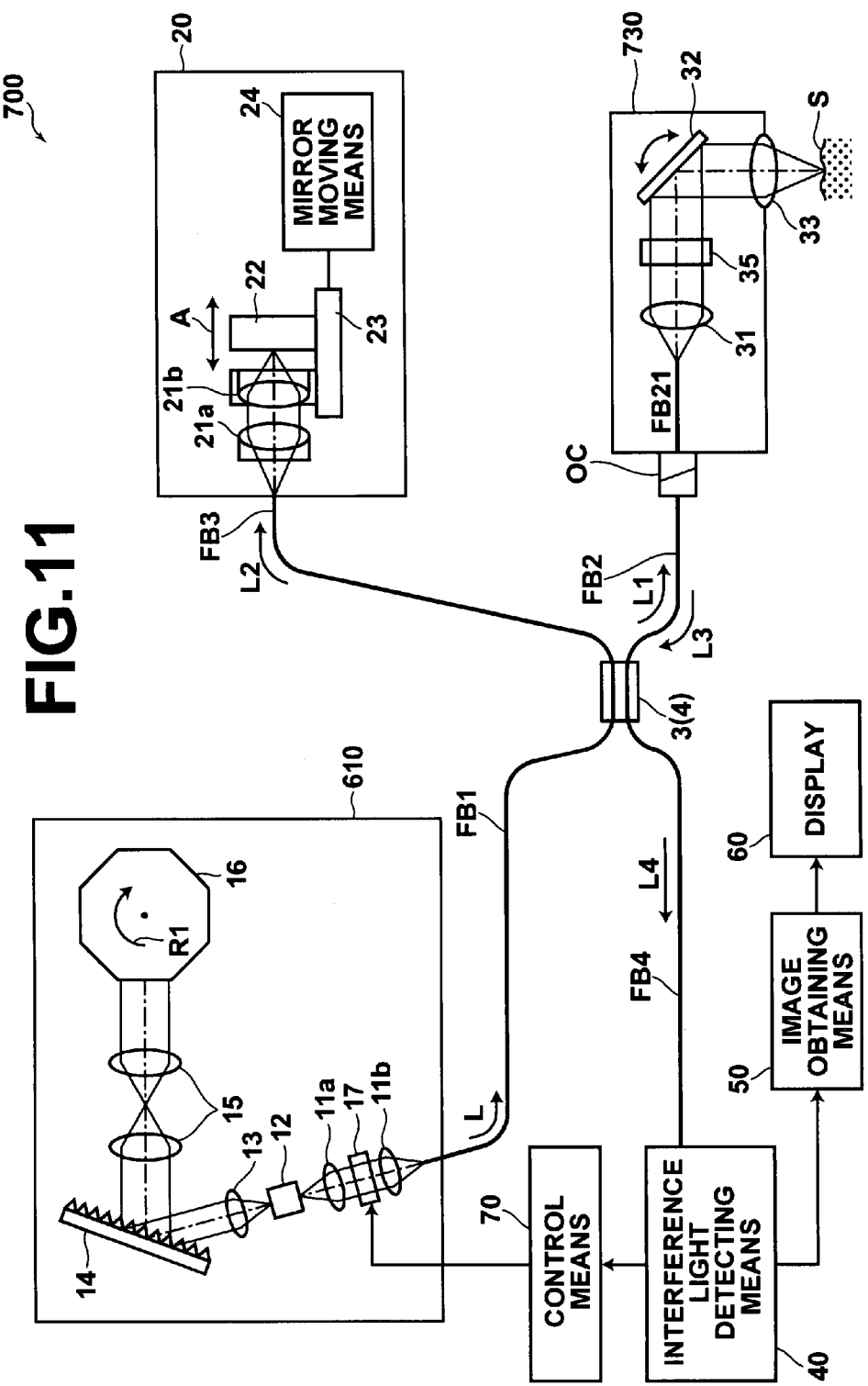
FIG. 11 is a view showing an optical tomography system in accordance with a seventh embodiment of the present invention.

In the optical tomography system 700, a probe 730 is employed instead of the probe 30 of the optical tomography system 600 of FIG. 10. The probe 730 differs from the probe 30 of the optical tomography system 600 of FIG. 10 in that a ¼λ plate 35 is disposed between the collimating lens 31 and the scanning mirror 32. That is, in the optical tomography system 700, a ¼λ plate is disposed at each of the two places in the light source unit 610 and the probe 730.

In the optical tomography system 700 in accordance with the seventh embodiment described above, effects similar to those in the optical tomography system 100 in accordance with the first embodiment can be obtained and the influence of the polarization characteristics can be suppressed, whereby an optical tomographic image of an excellent quality can be obtained. Further, since the ¼λ plates are disposed at the two places in the optical tomography system 700, the influence of the polarization characteristics can be less.

Though a λ plate is provided in the light source unit or in the probe in the sixth and seventh embodiments, the present invention need not be limited to such arrangements the λ plate may be provided in at least one of the light source unit, the optical path from the light source unit to the light dividing means, the optical path from the light dividing means to the probe, the optical path from the optical connector OC in the probe to the object, and the optical path from the light dividing means to the combining means by way of the optical path length adjusting means, and may be provided at each of a plurality of places in these positions.

Though examples where a ¼λ plate is employed has been described in the sixth and seventh embodiments, the plate need not be limited to the ¼λ plate but a plate which gives a phase difference of other than a quarter wavelength may be employed. For example, linearly polarized light can be converted to elliptically polarized light even if a ⅛λ plate or a ⅝λ plate is employed and the ⅛λ plate or the ⅝λ plate may be employed.

Though examples where a polarization-preserving fiber or a ¼λ plate is rotatable about the optical axis and a control means which adjusts the rotating angle of the element is provided have been described in the above first to seventh embodiments, such a structure is unnecessary only to convert linearly polarized light to non-linearly polarized light. When the polarization-preserving fiber is employed, incident linearly polarized light can be converted to non-linearly polarized light by suitably setting the angle which the axis of polarization thereof makes to the direction of polarization of the incident linearly polarized light and the length of the polarization-preserving fiber. When the λ plate is employed, incident linearly polarized light can be converted to non-linearly polarized light by suitably setting the angle which the axis of polarization thereof makes to the direction of polarization of the incident linearly polarized light. However, a more excellent tomographic image can be obtained when the above described structure where the element is rotatable about the optical axis and a control means which adjusts the rotating angle of the element is provided is employed, since an excellent state of polarization of light can be obtained and fluctuation in the state of polarization of light and the like can be dealt with.

Though in the first to seventh embodiments, the control means controls a polarization-preserving fiber or a λ plate in the light source unit, the optical path from the light source unit to the light dividing means or the optical path from the light dividing means to the probe, the present invention need not be limited to such a control means. For example, a polarization-preserving fiber or a λ plate disposed in the probe 30 may be rotated and the rotating angle thereof may be controlled by a known control means.

Though in the first to seventh embodiments, the control means controls a single polarization-preserving fiber or a single λ plate, when the polarization changing means comprises a plurality of polarization-preserving fibers or a plurality of λ plates, the control means may control a plurality of polarization-preserving fibers or a plurality of λ plates.

Figure 12:
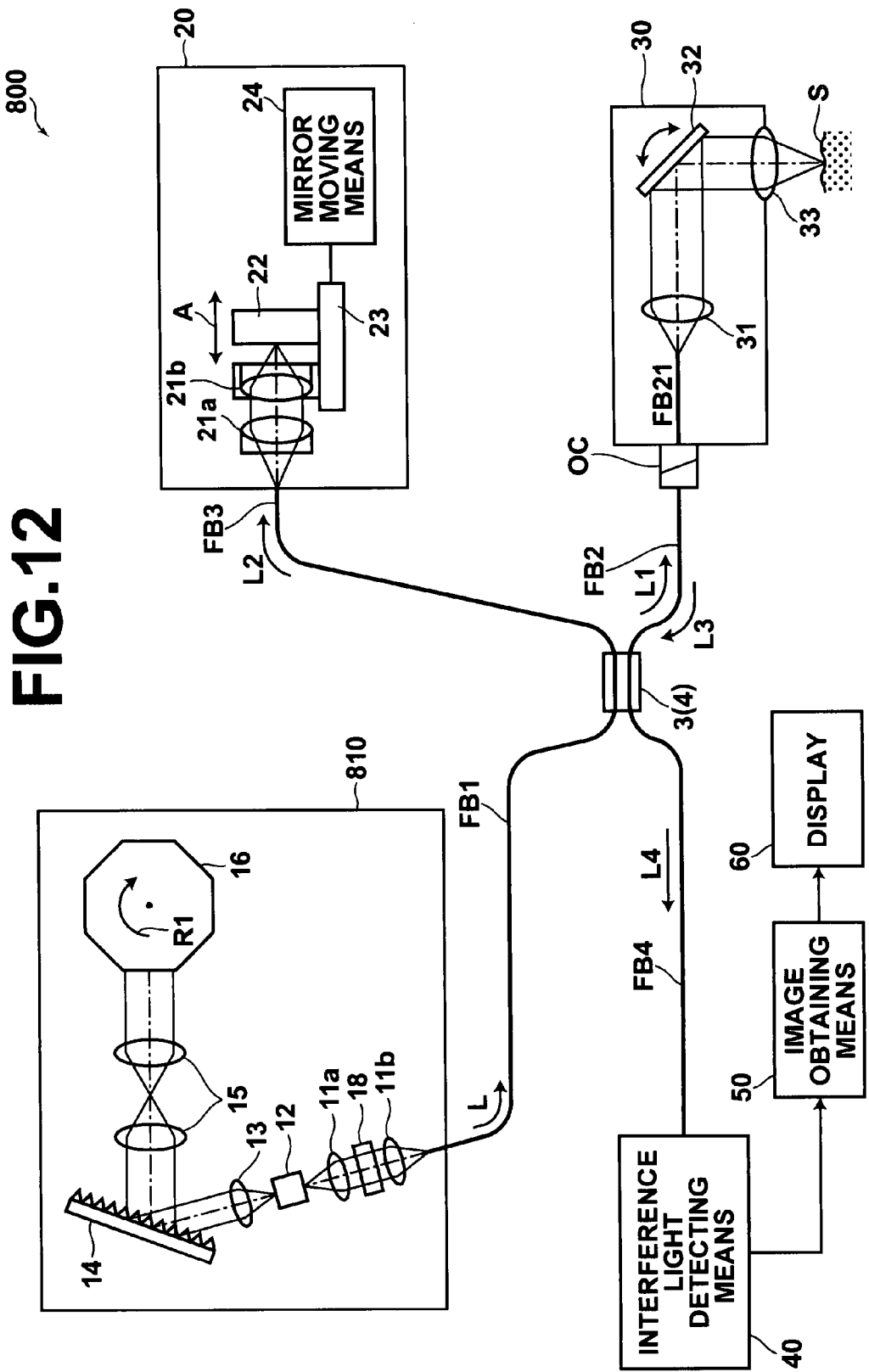
FIG. 12 is a view showing an optical tomography system in accordance with an eighth embodiment of the present invention.

An optical tomography system in accordance with an eighth embodiment of the present invention will be described with reference to FIG. 12, hereinbelow. The optical tomography system 800 in accordance with an eighth embodiment of the present invention is characterized in that a polarization releasing plate is employed as the polarization changing means. In the optical tomography system 800, a light source unit 810 where a polarization releasing plate 18 is employed as the polarization changing means in place of the ¼λ plate 17 of the light source unit 610 of FIG. 10 is employed in place of the light source unit 610. The elements analogous to those in the tomography system 600 of FIG. 10 are given the same reference numerals and the description thereof is abbreviated in the tomography system 800 of FIG. 12.

The polarization releasing plate 18 of the light source unit 810 of the optical tomography system 800 converts all light to non-polarized light. As the polarization releasing plate 18, for instance, those comprising a pair of anisotropic crystalline plates laminated together so that their optical axes is in perpendicular to each other and turning all light to non-polarized light as the whole beam system have been known.

Accordingly, in the optical tomography system 800 in accordance with the eighth embodiment described above, effects similar to those in the optical tomography system 100 in accordance with the first embodiment can also be obtained and the influence of the polarization characteristics can be suppressed, whereby an optical tomographic image of an excellent quality can be obtained. Further, in the optical tomography system 800, the influence of the polarization characteristics can be almost nullified since the polarization releasing plate 18 is employed.

Though a polarization releasing plate 18 is disposed in the light source unit in the eighth embodiment described above, the present invention need not be limited to such an arrangement but the polarization releasing plate 18 may be provided in at least one of the light source unit, the optical path from the light source unit to the light dividing means, the optical path from the light dividing means to the probe, the optical path from the optical connector OC in the probe to the object, and the optical path from the light dividing means to the combining means by way of the optical path length adjusting means, and may be provided at each of a plurality of places in these positions.

Though, in the description of the first to eighth embodiments, the light incident to the polarization changing means is linearly polarized light, when the incident light is not of perfect linearly polarized light polarized in one direction but comprises a mixture of a plurality of linearly polarized lights the directions of polarization of which are different from each other or a mixture of linearly polarized lights and non-linearly polarized lights, the present invention may be applied with a most intense linearly polarized light taken as the incident light to the polarization changing means.

Though, in the description of the first to eighth embodiments, the polarization changing means is a polarization-preserving fiber, a wavelength plate or a polarization releasing plate, a plurality of kinds of the polarization changing means may be provided together in a single optical tomography system.

Though in the above description, an SS-OCT system is illustrated by way of example in the first embodiment, and an SD-OCT system and a TD-OCT system applied with features of the first embodiment are respectively illustrated as second and third embodiments. The features of the fourth to eighth embodiments may be similarly applied to an SD-OCT system and a TD-OCT system.

What is claimed is:

1. An optical tomography system for obtaining a tomographic image of an object comprising
   a light source unit which emits light,
   a light dividing means which divides the light emitted from the light source unit into measuring light and reference light,
   a combining means which combines the reflected light from the object when the measuring light is projected onto the object and the reference light,
   an interference light detecting means which detects interference light of the reflected light and the reference light which have been combined by the combining means, and
   an image obtaining means which obtains a tomographic image of the object on the basis of the interference light detected by the interference light detecting means,
   wherein the improvement comprises that a polarization changing means which converts linearly polarized light to non-linearly polarized light is provided in at least one of the light source unit, the optical path from the light source unit to the light dividing means, the optical path of the measuring light from the light dividing means to the object, the optical path of the reflected light from the object to the combining means and the optical path of the reference light from the light dividing means to the combining means,
   wherein, the polarization changing means comprises a polarization-preserving optical fiber which is disposed so that the direction of polarization of the linearly polarized light and the direction of axis of polarization of the linearly polarized light differ from each other,
   wherein at least one of the polarization-preserving optical fibers is rotatable about the optical axis and a control means which controls the rotating angle of the rotatable polarization-preserving optical fiber according to the result of the detection by the interference light detecting means is further provided.

2. An optical tomography system for obtaining a tomographic image of an object comprising
   a light source unit which emits light,
   a light dividing means which divides the light emitted from the light source unit into measuring light and reference light,
   a combining means which combines the reflected light from the object when the measuring light is projected onto the object and the reference light,
   an interference light detecting means which detects interference light of the reflected light and the reference light which have been combined by the combining means, and
   an image obtaining means which obtains a tomographic image of the object on the basis of the interference light detected by the interference light detecting means,
   wherein the improvement comprises that a polarization changing means which converts linearly polarized light to non-linearly polarized light is provided in at least one of the light source unit, the optical path from the light source unit to the light dividing means, the optical path of the measuring light from the light dividing means to the object, the optical path of the reflected light from the object to the combining means and the optical path of the reference light from the light dividing means to the combining means,
   wherein, the polarization changing means comprises at least two polarization-preserving optical fibers which are disposed to be different from each other in the direction of axis of polarization,
   wherein at least one of the polarization-preserving optical fibers is rotatable about the optical axis and a control means which controls the rotating angle of the rotatable polarization-preserving optical fiber according to the result of the detection by the interference light detecting means is further provided.

3. An optical tomography system for obtaining a tomographic image of an object comprising
   a light source unit which emits light,
   a light dividing means which divides the light emitted from the light source unit into measuring light and reference light,
   a combining means which combines the reflected light from the object when the measuring light is projected onto the object and the reference light,
   an interference light detecting means which detects interference light of the reflected light and the reference light which have been combined by the combining means, and
   an image obtaining means which obtains a tomographic image of the object on the basis of the interference light detected by the interference light detecting means,
   wherein the improvement comprises that a polarization changing means which converts linearly polarized light to non-linearly polarized light is provided in at least one of the light source unit, the optical path from the light source unit to the light dividing means, the optical path of the measuring light from the light dividing means to the object, the optical path of the reflected light from the object to the combining means and the optical path of the reference light from the light dividing means to the combining means
   wherein, the polarization changing means comprises a wavelength plate, wherein the wavelength plate is rotatable about the optical axis and a control means which controls the rotating angle of the rotatable wavelength according to the result of the detection by the interference light detecting means is further provided.

4. An optical tomography system for obtaining a tomographic image of an object comprising a light source unit which emits light, a light dividing means which divides the light emitted from the light source unit into measuring light and reference light, a combining means which combines the reflected light from the object when the measuring light is projected onto the object and the reference light, an interference light detecting means which detects interference light of the reflected light and the reference light which have been combined by the combining means, and an image obtaining means which obtains a tomographic image of the object on the basis of the interference light detected by the interference light detecting means, wherein the improvement comprises that a polarization changing means which converts linearly polarized light to non-linearly polarized light is provided in at least one of the light source unit, the optical path from the light source unit to the light dividing means, the optical path of the measuring light from the light dividing means to the object, the optical path of the reflected light from the object to the combining means and the optical path of the reference light from the light dividing means to the combining means wherein the polarization changing means comprises at least two wavelength plates which are disposed to be different from each other in the direction of axis of polarization, wherein at least one of the wavelength plates is rotatable about the optical axis and a control means which controls the rotating angle of the rotatable polarization-preserving optical fiber according to the result of the detection by the interference light detecting means is further provided.

5. A method of adjusting quality of an image obtained by an optical tomography system for obtaining a tomographic image of an object comprising a light source unit which emits light, a light dividing means which divides the light emitted from the light source unit into measuring light and reference light, a combining means which combines the reflected light from the object when the measuring light is projected onto the object and the reference light, an interference light detecting means which detects interference light of the reflected light and the reference light which have been combined by the combining means, an image obtaining means which obtains a tomographic image of the object on the basis of the interference light detected by the interference light detecting means, and at least one polarization-preserving optical fiber which converts linearly polarized light to non-linearly polarized light and is provided in at least one of the light source unit, the optical path from the light source unit to the light dividing means, the optical path of the measuring light from the light dividing means to the object, the optical path of the reflected light from the object to the combining means and the optical path of the reference light from the light dividing means to the combining means to be rotatable about the optical axis, characterized by the step of, when the tomographic image of the object is obtained from the interference light detected by the interference light detecting means, changing the rotating angle of the polarization-preserving optical fiber, whereby the quality of the tomographic image to be obtained is changed.

6. A method of adjusting quality of an image obtained by an optical tomography system for obtaining a tomographic image of an object comprising a light source unit which emits light, a light dividing means which divides the light emitted from the light source unit into measuring light and reference light, a combining means which combines the reflected light from the object when the measuring light is projected onto the object and the reference light, an interference light detecting means which detects interference light of the reflected light and the reference light which have been combined by the combining means, an image obtaining means which obtains a tomographic image of the object on the basis of the interference light detected by the interference light detecting means, and at least one wavelength plate which converts linearly polarized light to non-linearly polarized light and is provided in at least one of the light source unit, the optical path from the light source unit to the light dividing means, the optical path of the measuring light from the light dividing means to the object, the optical path of the reflected light from the object to the combining means and the optical path of the reference light from the light dividing means to the combining means to be rotatable about the optical axis, characterized by the step of, when the tomographic image of the object is obtained from the interference light detected by the interference light detecting means, changing the rotating angle of the wavelength plate, whereby the quality of the tomographic image to be obtained is changed.

* * * * *